United States Patent
Morley

(10) Patent No.: US 10,323,275 B2
(45) Date of Patent: Jun. 18, 2019

(54) METHODS FOR SEQUENCING A POLYNUCLEOTIDE STRAND

(71) Applicant: DNAE GROUP HOLDINGS LTD, London (GB)

(72) Inventor: Daniel Morley, London (GB)

(73) Assignee: DNAE Group Holdings Limited, London (GB)

( * ) Notice: Subject to any disclaimer, the term of this patent is extended or adjusted under 35 U.S.C. 154(b) by 206 days.

(21) Appl. No.: 15/306,607

(22) PCT Filed: Apr. 27, 2015

(86) PCT No.: PCT/GB2015/051215
§ 371 (c)(1),
(2) Date: Oct. 25, 2016

(87) PCT Pub. No.: WO2015/162438
PCT Pub. Date: Oct. 29, 2015

(65) Prior Publication Data
US 2017/0044604 A1    Feb. 16, 2017

(30) Foreign Application Priority Data

Apr. 25, 2014 (GB) .................................. 1407334.0
Mar. 2, 2015 (GB) .................................. 1503465.5

(51) Int. Cl.
*C12P 19/34* (2006.01)
*C12Q 1/6869* (2018.01)
*G16B 30/00* (2019.01)

(52) U.S. Cl.
CPC ........... *C12Q 1/6869* (2013.01); *G16B 30/00* (2019.02)

(58) Field of Classification Search
None
See application file for complete search history.

(56) References Cited

U.S. PATENT DOCUMENTS

| | | | | |
|---|---|---|---|---|
| 8,901,043 | B2 * | 12/2014 | Eckhardt | ............ C12N 15/1089 435/6.1 |
| 2013/0178374 | A1 | 7/2013 | Eckhardt et al. | |
| 2013/0311105 | A1 * | 11/2013 | Chen | ............ G06F 19/12 702/20 |
| 2014/0003123 | A1 | 1/2014 | Karpov et al. | |
| 2014/0031238 | A1 * | 1/2014 | Schultz | ............ C12Q 1/6874 506/2 |
| 2014/0296080 | A1 * | 10/2014 | Hubbell | ............ G06F 19/22 506/2 |

FOREIGN PATENT DOCUMENTS

WO   2011156707 A2   12/2011

OTHER PUBLICATIONS

International Search Report and Opinion dated Jul. 20, 2015 in corresponding Application No. PCT/GB2015/051215; 14 pgs.
Ahmadian et al., "Single-nucleotide polymorphism analysis by pyrosequencing.", Analytical Biochemistry, Academic Press Inc, New York, Apr. 10, 2000; 280(1)103-110., 8 pgs.
Daniel Ramon et al., "Pyrosequencing™: A one-step method for high resolution HLA typing", Journal of Translation Medicine, Biomed Central, London, GB, Nov. 26, 2003; 10 pgs.
Jonas Binladen et al., "The Use of Coded PCR Primers Enables High-Throughput Sequencing of Multiple Homolog Amplification Products by 454 Parallel Sequencing", PLoS One, Public Library of Science, US, vol. 2, No. 2, Jan. 1, 2007, 10 pgs.
Search Report dated Nov. 26, 2015 in corresponding Application No. GB1503465.5; 4 pgs.
Mats Carlsson and Nicolas Beldiceanu, "Multiplex dispensation order generation for pyrosequencing." In CP'2004 Norkshop on CSP Techniques with Immediate Application, 2004., 16 pgs.
Mats Carlsson and Nicolas Beldiceanu, "Dispensation order generation for pyrosequencing." In Yi-Ping Phoebe Chen, editor, Proc. APBC2004, vol. 29 of Conferences in Research and Practice in Information technology, Dunedin, New Zealand, 2004. Australian Computer Society, 6 pgs.

* cited by examiner

*Primary Examiner* — Kenneth R Horlick
(74) *Attorney, Agent, or Firm* — Maier & Maier, PLLC

(57) ABSTRACT

Described is a method for sequencing a polynucleotide strand by sequencing by synthesis, the method including selecting a predetermined order of nucleotides to provide to a sequencing reaction, the order being selected to correlate with a predicted sequence for the polynucleotide strand; monitoring the reaction to detect incorporation of a nucleotide into a synthesized polynucleotide strand; wherein, in the event that nucleotide incorporation is detected, proceeding to provide the next nucleotide in the predetermined order. In the event that nucleotide incorporation is not detected, the predicted sequence for the polynucleotide strand may be revised and a new predetermined order of nucleotides selected, wherein the new predetermined order is selected to correlate with the revised predicted sequence. In this way, the sequencing reaction provides feedback to modify the order of nucleotides provided, thereby improving the efficiency of the sequencing reaction.

17 Claims, No Drawings
Specification includes a Sequence Listing.

METHODS FOR SEQUENCING A POLYNUCLEOTIDE STRAND

FIELD OF THE INVENTION

The present invention relates to methods for sequencing polynucleotide strands using a sequencing by synthesis method; and in particular to methods having an improved or optimised order of nucleotide flow. Aspects of the invention relate to methods for improving or optimising the order of nucleotide flow in sequencing by synthesis methods.

BACKGROUND TO THE INVENTION

Sequencing by synthesis methods are commonly used in next generation sequencing (NGS) technologies. Nucleotide strands complementary to a target polynucleotide fragment are extended by incorporation of nucleotides (eg, dNTPs) by a polymerase enzyme, and the incorporation is detected; for example, by fluorescence or by detection of hydrogen ions released during polymerisation. This latter technique is used in ion semiconductor sequencing methods. Incorporation of a given dNTP into a strand means that the complementary nucleotide is present at that position in the template strand.

In some techniques, different nucleotides are given different detectable labels, so that the specific nucleotide incorporated can be determined. However, an alternative approach is simply to add a single type of nucleotide at a time to the polymerase reaction; if incorporation of the nucleotide is detected, then the complementary nucleotide in the template strand is known. Typically a sequencing reaction will cycle through all four nucleotides in order, and repeat this for the duration of the sequencing. However, this imposes time limitations on the process, since it is necessary to repeat the cycle multiple times in order to obtain the sequence, and depending on the order of nucleotides in the template strand, as much as four nucleotide flows may be necessary to obtain information on a single base.

However, for many applications of sequencing by synthesis technology, the expected sequence of the template is known, or at least partially known. For example, a patient sample may be analysed for the presence of a suspected pathogen, whereby a sequence diagnostic for a given pathogen is detected. In this example, the sequence to be detected is already known. Alternatively, for example, variants in certain gene sequences may be detected in order to determine the presence or absence of a given polymorphism or mutation. Here again at least a portion of the sequence is known. In certain applications of sequencing by synthesis, polynucleotide fragments are prepared for sequencing by ligating or otherwise incorporating adapters of known sequence, to which sequencing primers can bind. At least this part of the sequencing reaction may benefit from the knowledge of the region to be sequenced.

US2014/0031238 describes use of alternate nucleotide flow ordering which is not simply a continuous repeat of all four nucleotides. This alternate ordering is said to address potential problems with loss of phasic synchrony resulting from incomplete extension. There is no suggestion that the order of nucleotide flow may be modified by taking advantage of the existence of known sequences.

It would be advantageous to provide a sequencing by synthesis method whereby the order of nucleotide flow may be improved or optimised. In certain embodiments this is achieved using a priori knowledge of the sequence to be detected. In other embodiments, likely candidate sequences may be selected, and the nucleotide flow determined based on the likelihood of certain sequences being present. In yet further embodiments, a feedback mechanism may be used to modify the nucleotide flow during sequencing by synthesis.

BRIEF SUMMARY OF THE INVENTION

According to a first aspect of the present invention, there is provided a method for sequencing a polynucleotide strand by sequencing by synthesis, the method comprising the steps of:

a) providing in a reaction a polynucleotide strand to be sequenced, a primer, and a polymerase enzyme;
b) providing to the reaction nucleotides in a predetermined order, wherein the predetermined order is selected to correlate with a predicted sequence for the polynucleotide strand;
c) monitoring the reaction to detect incorporation of a nucleotide into a synthesised polynucleotide strand;
wherein, in the event that nucleotide incorporation is detected, proceeding to provide the next nucleotide in the predetermined order.

The method may further comprise wherein, in the event that nucleotide incorporation is not detected, revising the predicted sequence for the polynucleotide strand and selecting a new predetermined order of nucleotides, wherein the new predetermined order is selected to correlate with the revised predicted sequence.

As an alternative to revising the predicted sequence and continuing with synthesis, the reaction may simply be stopped. This may be desirable where sequencing is being used to determine the presence of a specific predicted sequence (hence if it is not present, the reaction may be stopped), or where several likely candidate predicted sequences have been tested. A still further alternative to stopping the reaction would be to select a new predetermined order of nucleotides which represents multiple cycles of all four nucleotides (for example, A, C, G, T, repeated). This may be advantageous where several likely candidate predicted sequences have been tested, and the actual sequence is still unknown; hence the sequencing can revert to a simple repetitive cycle of the four nucleotides.

Thus, in the present method, the order in which nucleotides are provided to the reaction is selected based on knowledge of the polynucleotide to be sequenced. If the predicted sequence is correct, then nucleotide synthesis will occur each time a nucleotide is provided (allowing for synthesis errors, and assuming that the predetermined order is perfectly complementary to the predicted sequence). Detection of nucleotide incorporation confirms that the predicted sequence is correct, and the next nucleotide is provided. If nucleotide incorporation is not detected, then (again, allowing for synthesis errors) the predicted nucleotide sequence is incorrect. The predicted sequence may then be revised to take account of the error, and the order of nucleotides modified accordingly.

The present method is therefore adaptive, in that it makes use of feedback from the synthesis reaction in order to inform and modify the order in which nucleotides are provided. This allows the expected rate of incorporation of nucleotides to rise from 1 in 4 (where, of every 4 nucleotide flows, only one is correct) to higher; as much as 1 in 1 where the sequence is perfectly predicted—although in practice less. This can not only reduce the time needed to perform a sequencing operation, but can also reduce the amount of reagents necessary.

The nucleotides are preferably dNTPs; more preferably four different dNTPs are provided (A, C, G, T).

The term "selected to correlate" preferably means that the order of nucleotides matches that of a sequence complementary to that of the predicted polynucleotide sequence. By "complementary" is preferably meant "perfectly complementary", although there may be circumstances in which somewhat less than 100% complementarity is used.

The predicted polynucleotide sequence may be predicted based on a priori information. For example, the sequence may be predicted based on knowledge of sequences which are likely to be detected. As an example, in a clinical setting where a patient is suspected of having a bacterial or other infection, knowledge of the clinical situation—such as symptoms, recent medical history, or any other patient detail—may make certain particular infections more likely than others. The predicted sequence may be determined based on this information. For example, if a patient is suspected of having an MRSA infection, then the predicted sequence may be selected to be diagnostic of MRSA infection. Several different infections may be considered possible, but with different probabilities. Thus, the method may comprise the step of determining the initial relative likelihood of a plurality of predicted sequences, and selecting the initial predicted sequence to be the most likely of the plurality of predicted sequences. The method may further comprise the step of, when revising the predicted sequence, selecting the next most likely of the plurality of predicted sequences as the revised predicted sequence. In this way, several possibilities may be considered and confirmed or rejected.

Alternatively, or in addition, the predicted sequence may be based on a known sequence of interest. For example, if an assay is being carried out to detect presence or absence of a specific organism, then a polynucleotide sequence diagnostic of that organism may be used as the predicted sequence. This may also be extended to cover a range of different organisms—for example, the 16S and 23S ribosomal genes may be diagnostic of a number of different organisms, and one or the other or both may be used as an initial predicted sequence. This can be combined with the previous embodiment in which a most likely sequence is initially selected, and this is then revised to the next most likely predicted sequence in the event of non-detection of nucleotide incorporation. Many other diagnostic sequences may be used; for example, oncogenes, bacterial toxins.

In certain embodiments, the step of monitoring the reaction to detect incorporation of a nucleotide may also include, in the event that incorporation is detected, adding data representing that nucleotide to recorded sequence data representing the polynucleotide to be sequenced. The data representing the nucleotide may represent the complement of that nucleotide. This allows sequence information to be recorded as sequencing proceeds. In the event that nucleotide incorporation is not detected, data representing the absence of that nucleotide (or its complement) from the sequence may also be added to the recorded sequence data.

The step of revising the predicted sequence data may include comparing the recorded sequence data (including, where relevant, the information of absence of a given nucleotide) to polynucleotide sequence data stored in a database, and selecting the most likely candidate sequence from the database matching the recorded sequence data as a revised predicted sequence. The database may be a remote database; for example, accessible via a computer network such as the internet; it may be publicly available (eg, the GenBank sequence database). Alternatively, the database may be a local database; for example, stored within a local computer memory or a local data storage device. The database may represent a restricted subset of sequence information such as only those sequences considered likely to be of interest. For example, a database may include only 16S and 23S sequence data from common pathogens; use of a restricted database can reduce time taken to compare the recorded sequence data with the sequence data in the database.

The method may further comprise, prior to step (b), providing multiple different nucleotides to the reaction simultaneously. The multiple different nucleotides may lack one, or two, of the four nucleotides. This allows rapid extension of a region of the polynucleotide sequence, until a missing nucleotide is encountered. This aspect of the method may be of use where a region of sequence is known, but is not considered informative or of interest to the purpose of the sequencing; the missing nucleotide(s) may be selected to allow sequence extension up to, or close to, the region of interest. In this way regions not of interest may be rapidly bypassed. A region of known sequence which is not of interest may include, for example, adapter sequences, or highly conserved regions of genes. The multiple different nucleotides to be provided may be selected based on the known region not of interest, in order to ensure that rapid synthesis terminates before the region of interest is reached. Multiple rounds of providing multiple different nucleotides may be used.

The method may be used in circumstances where a single polynucleotide sequence is to be sequenced; or where multiple different polynucleotide sequences are to be sequenced. In the latter circumstance, the predetermined order of nucleotides may be selected to correlate with predicted sequences for two or more, preferably all, of the multiple different polynucleotide sequences. Preferably the order of nucleotides is selected to allow efficient sequencing of each of the two or more different polynucleotide sequences. "Efficient" may be defined as an order of nucleotides which provides an improved ratio of bases incorporated to nucleotides provided across all the sequences under consideration, compared with an order in which all four bases are cycled in a repetitive fashion (eg, A, C, G, T repeated). For example, the different sequences may be compared and a consensus sequence determined; the order of nucleotides may correspond with the consensus sequence (or its complement). Other methods of determining the order of nucleotides may be used. The order need not provide the most efficient sequencing, since the most efficient order may not be possible for other practical reasons. The term "optimised" is also used herein to refer to a sequence which provides efficient sequencing; again "optimised" does not imply that the sequence provides the most efficient sequencing. Thus, some sequences may be more optimised than others.

A further aspect of the present invention provides a method for optimising the order of nucleotides provided in a sequencing by synthesis reaction, the method comprising the steps of:
  a) determining a predicted sequence for a polynucleotide to be sequenced; and
  b) determining a predetermined order for nucleotides to be provided to a sequencing reaction, wherein the predetermined order is selected to correlate with a predicted sequence for the polynucleotide strand.

The method may further comprise the steps of:
  c) determining an actual sequence for the polynucleotide strand, by providing nucleotides to a sequencing reaction including the polynucleotide to be sequenced;
  d) comparing the predicted sequence to the actual sequence; and e) in the event that the predicted sequence differs from the actual sequence, revising the predicted sequence for the polynucleotide strand based on the actual sequence and selecting a new predetermined order of nucleotides, wherein the new predetermined order is selected to correlate with the revised predicted sequence.

Other features of this aspect of the invention are as for the first aspect, described above.

A still further aspect of the present invention provides a method for sequencing a polynucleotide strand by sequencing by synthesis, the method comprising the steps of:
a) providing in a reaction a polynucleotide strand to be sequenced, a primer, and a polymerase enzyme;
b) providing to the reaction multiple different nucleotides simultaneously, wherein the multiple different nucleotides lack at least one of the four nucleotides A, C, G T;
c) subsequently providing to the reaction nucleotides in a predetermined order, wherein the predetermined order is selected to correlate with a predicted sequence for the polynucleotide strand; and
d) monitoring the reaction to detect incorporation of the nucleotides of the predetermined order into a synthesised polynucleotide strand.

The method may further comprise the steps of:
e) in the event that nucleotide incorporation is detected, proceeding to provide the next nucleotide in the predetermined order; or
f) in the event that nucleotide incorporation is not detected, revising the predicted sequence for the polynucleotide strand and selecting a new predetermined order of nucleotides, wherein the new predetermined order is selected to correlate with the revised predicted sequence.

In certain embodiments, the step of monitoring the reaction to detect incorporation of a nucleotide may also include, in the event that incorporation is detected, adding data representing that nucleotide to recorded sequence data representing the polynucleotide to be sequenced. The data representing the nucleotide may represent the complement of that nucleotide. This allows sequence information to be recorded as sequencing proceeds. In the event that nucleotide incorporation is not detected, data representing the absence of that nucleotide (or its complement) from the sequence may also be added to the recorded sequence data.

The step of revising the predicted sequence data may include comparing the recorded sequence data (including, where relevant, the information of absence of a given nucleotide) to polynucleotide sequence data stored in a database, and selecting the most likely candidate sequence from the database matching the recorded sequence data as a revised predicted sequence. The database may be a remote database; for example, accessible via a computer network such as the internet; it may be publicly available (eg, the GenBank sequence database). Alternatively, the database may be a local database; for example, stored within a local computer memory or a local data storage device. The database may represent a restricted subset of sequence information such as only those sequences considered likely to be of interest. For example, a database may include only 16S and 23S sequence data from common pathogens; use of a restricted database can reduce time taken to compare the recorded sequence data with the sequence data in the database.

A yet further aspect of the present invention provides a method for sequencing a polynucleotide strand by sequencing by synthesis, the method comprising the steps of:

a) providing in a reaction a plurality of different polynucleotide strands to be sequenced, one or more primers, and a polymerase enzyme;
b) providing to the reaction nucleotides in a predetermined order, wherein the predetermined order is selected to correlate with predicted sequences for the plurality of different polynucleotide strands; and
c) monitoring the reaction to detect incorporation of the nucleotides of the predetermined order into synthesised polynucleotide strands;
wherein the predetermined order of nucleotides is selected to allow efficient sequencing of each of the plurality of different polynucleotide sequences.

"Efficient" may be defined as an order of nucleotides which provides an improved ratio of bases incorporated to nucleotides provided across all the sequences under consideration, compared with an order in which all four bases are simply cycled (eg, A, C, G, T repeated). For example, the different sequences may be compared and a consensus sequence determined; the order of nucleotides may correspond with the consensus sequence (or its complement). Other methods of determining the order of nucleotides may be used. The order need not provide the most efficient sequencing, since the most efficient order may not be possible for other practical reasons.

DETAILED DESCRIPTION OF THE INVENTION

The invention relates to reducing the time taken to determine the nucleotide sequence of a particular polynucleotide sample through alteration of the sequence of nucleotide delivery. Typically in sequencing by synthesis methods, nucleotides are provided individually to the sequencing reaction in a fixed order (for example, A, C, G, T); if the next nucleotide to be added to the strand being synthesised is present then the strand will be extended, and the extension detected. Unused nucleotides are washed from the reaction, and the next nucleotide in the sequence added. Sequencing DNA using ISFET sensors generally involves the sequential flow of nucleotides (T,G,C,A) on the chip. If the particular nucleotide flushed across the chip finds its complement nucleotide on the template strand, then a hydrogen ion is liberated and detected by the ISFET sensor as a change in mV. In general, each individual sensor detects the hydrogen ions released from a clonal population of DNA template, which may be generated through a clonal amplification technique such as emPCR, and immobilised on a bead within a well. Each clonal population may contain many millions of identical DNA copies.

It is reported in the literature that when using a standard 4-nucleotide cycle, a random DNA sequence will extend by approximately 2.4 bases per cycle. This is because not every nucleotide flow has a corresponding complementary base on the template strand, resulting in approximately 40% flows returning null, or 0-mer, results.

The inventors describe herein a number of approaches which may be used to optimise the order of nucleotides delivered to the growing strand, and hence reduce time taken to sequence a sample. The approaches are described herein individually, but it will be appreciated that one or more may be used in combination. The invention is intended to reduce the time taken to sequence a particular targeted sample. The sequence may allow sequence of a certain length to be read in a shorter time, or allow longer read-lengths in the same time period. All approaches share the common feature that the order of nucleotides to be provided to the reaction is determined in advance, based on some knowledge of the sample to be sequenced. In certain of the approaches, the order of nucleotides may be modified during sequencing, based on the results of the sequencing so far. The order of nucleotides may be selected a priori based on a probabilistic algorithm, taking into account various clinical factors.

By tailoring the nucleotide flow to match a predicted sequence, the efficiency of each flow event is increased up to 100%, in the case that the correct sequence is predicted.

In one example of the invention, the sample of interest may be a targeted sequence, where assumptions can be made about the probability of the sample matching a certain sequence. For instance, in a clinical setting where other patient data may feed into the system to determine the likely presence of certain infectious agents. In another example, the sequence of nucleotide delivery to the chip may be intelligently determined and updated throughout the course of a test, depending on feedback regarding the DNA sequence that has already been established.

The invention is considered of particular relevance when the sample is targeted to a particular genetic region, as opposed to de novo or very high-throughput DNA sequencing. Assumptions can be made regarding the probability of the sample sequence matching a known reference sequence.

For a targeted sequencing application, there is scope to improve performance by reducing the time taken to perform the test. Due to the fact that targeted sequences may be known, or can be predicted to a certain degree, the nucleotide flow pattern may be tailored to increase the throughput and efficiency of the test. Four main ways are identified in which this concept may be applied, as discussed in this document:

1. Predictive nucleotide flow
2. Adaptive nucleotide flow
3. Multi-nucleotide flow
4. Optimised flow for multiple templates The invention could be implemented in several ways, as presented below.

1) Predictive Sequence Flow

In the case that it is possible to make a probability assessment prior to running the test regarding the particular sample under interrogation. This may include both 'unknown' regions of samples, and 'known' regions such as primer sequences used for pre-amplification or library preparation. The probability assessment may include further clinical patient data obtained from various other sources, which is then input into the sequencing instrument. The probability assessment may simply be undertaken by the physician (for example, on reviewing the patient history and symptoms, they conclude that an infection is most likely to be Bacteria #1, but that there is a lesser chance that the infection is Bacteria #2, or Bacteria #3). Alternatively, the probability assessment may make use of an expert system or similar automated means for determining relative likelihood of various infections.

An expert system may be implemented as a probability assessment performed on the sequencing instrument (or indeed as a separate system, for example, a computer system executing an appropriate computer program) to identify the 'most likely' infectious agent for a given patient.

Data input to instrument by clinician including, for example, relevant patient history (recent surgery or trauma, recent infections, medication etc.) and local nosocomial data (infectious disease profiles, recent antibiotic resistance outbreaks etc.)

Algorithm predicts most likely infectious agent based on input data, as in table below (which is merely an illustrative example).

Initial nucleotide flow tailored to exactly match that of predicted infectious agent.

| Infectious agent | Infection probability |
| --- | --- |
| Bacteria 1 | 50% |
| Bacteria 2 | 20% |
| Bacteria 3 | 10% |
| Bacteria 4 | 2% |
| Bacteria 5 | 2% |
| Bacteria 6 | <1% |

In an alternative, the physician may examine the patient and conclude that an infection is most likely to be caused by a first infectious agent, but that there is a smaller chance that the infection is due to second or third infectious agents (that is, without the use of an expert system or without directly assigning quantitative probabilities). In this case, the physician (or a technician) may input the list of three potential infectious agents directly into a sequencing instrument; the instrument will then take each of the three potential agents in order as the predicted infectious agent, and hence tailor the initial nucleotide flow to the first predicted agent.

In most cases, an informative gene may be selected for sequencing (for example, ribosomal genes from bacteria), and the sequence for this gene in the most likely predicted infectious agent used to determine the sequence of the initial nucleotide flow.

2) Adaptive Sequence Flow

Relies on real-time feedback from the sequencing instrumentation, and adapts the pattern of nucleotides accordingly. This would involve referencing (continuously, or at certain time points) the output data to a database, and adapting the future nucleotide flow pattern based on data already generated. This approach is useful in the case that less is known about the sequence under interrogation, or that the sequence predicted initially proves to be incorrect.

An adaptive sequence flow changes the flow pattern based on real-time feedback from the instrument.

EXAMPLE

The initial probability assessment is undertaken as described above, and the sequencing instrument determines the initial order of nucleotide flow, which order is tailored to the 'most likely' infectious agent. If the predicted sequence is incorrect, then the failure to extend the template is detected by the instrument, and a revised predicted sequence identified and used to determine a new order of nucleotide flow.

For example, the initial assessment gives the following probabilities:

| Infectious agent | Infection probability |
| --- | --- |
| Bacteria 1 | 50% |
| Bacteria 2 | 20% |
| Bacteria 3 | 10% |
| Bacteria 4 | 2% |
| Bacteria 5 | 2% |
| Bacteria 6 | <1% |

Infection is actually Bacteria #3. Algorithm incorrectly predicts Bacteria #1 based on probability assessment, and the instrument begins nucleotide flow tailored to Bacteria #1 sequence Bacteria #3: sample sequence

GCACCTGTCTCAGAGTTCCCGAAGGCACCAAAGCATC

Bacteria #1—based flow pattern

CGTGGACAGAGTGC

As each nucleotide extends the template upon the target strand, the instrument records data representing each nucleotide and the sequence of the target and/or synthesised strand.

Upon encountering the first mismatched base, the instrument cycles through nucleotides to find correct base:

Bacteria #3: sample sequence

GCACCTGTCTCAGAGTTCCCGAAGGCACCAAAGCATC

Bacteria #1

CGTGGACAGAGTG<u>T</u>

In this case, the nucleotide order predicted that a C would be the next base in the sequence, to match the Bacteria #1 sequence. However, the C did not extend the template sequence; thus, the instrument does not detect an extension event, and provides the remaining nucleotides (A, G, T) to determine which does extend the template. In this case, the T extends the template. This information is added to a record of the synthesised sequence. Based on the sequence obtained, the instrument compares the sequence obtained to date with the next most likely sequence—in this case, Bacteria #2—and if, as in this case, the next most likely sequence matches the synthesised strand so far, then the next most likely sequence becomes the new predicted sequence, and the nucleotide flow order is revised to correspond to the new predicted sequence. The instrument then restarts nucleotide flow tailored to Bacteria #2:

Bacteria #3: sample sequence

GCACCTGTCTCAGAGTTCCCGAAGGCACCAAGCATC

Bacteria #2—based flow pattern

CGTGGACAGAGTGTCAAGGGCTTCCGTGGTT<u>A</u>

Upon encountering a further mismatch (here, a G when the predicted sequence led to a flow order of A), the instrument again fails to detect an extension event and once more cycles through the remaining nucleotides to find the correct base insertion:

Bacteria #3: sample sequence

GCACCTGTCTCAGAGTTCCCGAAGGCACCAAGCATC

CGTGGACAGAGTGTCAAGGGCTTCCGTGGTT<u>C</u>

Based on the sequence obtained and the relative likelihoods of the various infectious agents, the algorithm revises the predicted sequence to that of Bacteria #3, and restarts nucleotide flow tailored to Bacteria #3.

Bacteria #3: sample sequence

GCACCTGTCTCAGAGTTCCCGAAGGCACCAAAGCATC

Bacteria #3—based flow pattern

CGTGGACAGAGTCTCAAGGGCTTCCGTGGTTTCGTAG

When the end of the synthesised sequence is reached with no further mismatches, the conclusion is made that the infection is Bacteria #3. The instrument ceases operation, and displays an output indicating the detected infection.

3) Multi-Nucleotide Flow

The approaches described above make use of methods providing a single nucleotide at a time in each flow event. This is preferable when it is the region of interest being sequenced, since it allows the detected sequence to be compared against the predicted sequence, and the predicted sequence revised if necessary. However, in many cases there will be at least some region not of interest which needs to be sequenced before the region of interest can be sequenced; for example, primers or adapters used to prepare samples for sequencing may be included in the samples to be analysed, and these regions are not informative as to the identity of the region of interest. Alternatively, highly conserved regions in genes may not be considered of interest, as they do not allow the user to distinguish between alternative sequences. By combining 2 or 3 nucleotides in a particular flow event, it is possible to 'fast-track' through a region of known sequence. For example, it may be possible to extend a known primer sequence in a very small number of flows, without extending the 'unknown' sequence of interest. This may be useful in extending regions that are highly conserved, for example in bacterial 16S and 23S rRNA genes, or in rarely mutated regions of human oncogenes.

As above, a 'probability assessment' may be performed to rank infectious agents in order of likelihood, and the order of nucleotides determined to match the sequence of the 'most likely' infectious agent. The nucleotide flow is begun based on this sequence.

The initial part of the sequence may be conserved among bacteria, for example

Bacteria 4

<u>CACCTGTC</u>ACTCTACTAACGTATGGCTACCCT

Bacteria 5

<u>CACCTGTC</u>CGAATGAGTATCTTATTACCATTG

Bacteria 6

<u>CACCTGTC</u>ATACGACGCATACGGTTCGAAACA

In this case, instead of flowing individual nucleotides to sequence the initial uninformative CACCTGTC portion, it is possible to 'fast-track' through the conserved region by mixing 2 or more nucleotides. This may be done using a dedicated reagent reservoir of mixed nucleotides, or by mixing nucleotides 'on-the-fly'

In standard nucleotide nomenclature:

"C and A" can be denoted by "M" (for a<u>M</u>ino containing nucleotides)

"T and G" can be denoted by "K" (for Keto-containing nucleotides")

In this example, an initial flow of M followed by K would extend 7 bases in the conserved region:

Bacteria 4

CACCTGTCACTCTACTAACGTATGGCTACCCT

Bacteria 5

CACCTGTCCGAATGAGTATCTTATTACCATTG

Bacteria 6

CACCTGTCATACGACGCATACGGTTCGAAACA

Multi-nucleotide flow M>>>K>>

While the instrument will detect that an extension event has occurred, it will not be apparent which nucleotide has extended the sequence. However, for this conserved region, that is not of concern. In some embodiments, three nucleotides may be provided together; for example, providing a mixture of A, C, and T will extend the initial sequence of CACCT, and stop at the subsequent G. Following this initial 'fast-track' through a known conserved region, the order of nucleotides could revert to a predictive or adaptive sequence, as discussed above, to continue the sequencing test.

4) Optimised Flow for Multiple Sequences

In many applications, there will be >1 sequence requiring sequencing. In this case, it is possible to create an algorithm to determine the most efficient nucleotide flow pattern to sequence all templates. Indeed, simulations show that when the flow pattern is optimised according to a basic algorithm, described below, the number of nucleotide flows required to sequence three 50 bp target templates can be reduced by as much as 28%.

As above, a 'probability assessment' may be performed to rank infectious agents in order of likelihood, and the order of nucleotides determined to match the sequence of the 'most likely' infectious agent. The nucleotide flow is begun based on this sequence.

There are scenarios when there will be >1 sequence under interrogation. For example, in an oncology application, there will likely be a number of oncogenes to be sequenced.

For bloodstream infections, if the test is required to deliver a detailed identification, there may be >1 genomic region under interrogation, even within a single organism.

The sequences below are representative of multiple sequences which may require simultaneous sequencing Sequence1

ACTCTACTAACGTATGGCTACCCTTAGTGGGGATGCTACCTAAAACCC
TTC

Sequence 2

CGAATGAGTATCTTATTACCATTTTGCAGTCCAATGTTTTAATTGTGTTG
T

Sequence 3

ATACGACGCATACGGTTCGAAACAAGAACGTACAATGTACGGAACTCGAC
A

Using a T, G, C, A cyclical flow pattern requires 100 flow events to sequence all three targets.

An optimum flow pattern sequences all templates in 72 flow events:

ACTGACTGACGTACGTATCGACTAGTCAGTACAGTGACTGAC

TACGTACTGATCGATCGATCGTCGATCGAT

28% reduction in flow duration

The optimum pattern may be determined as that pattern which minimises the number of flow events to sequence all templates of interest. Alternative definitions may be used.

In this scenario, the sequences do not resemble one another or share regions of significant homology. However, it is possible to determine a non-cyclical nucleotide flow pattern that completes extension of all sequences in the shortest possible time A predictive and adaptive algorithm used in conjunction with this aspect would further optimise the test and reduce duration.

Another example of multiple target regions, and the reduction in cycles needed to sequence all targets, is given by the following:

Representative target sequences:

Sequence 1
ACTCTACTAACGTATGGCTACCCTTAGTGGGGATGCTACCTAAAACCCTT
C

Sequence 2
CGAATGAGTATCTTATTACCATTTTGCAGTCCAATGTTTTAATTGTGTTG
T

Sequence 3
ATACGACGCATACGGTTCGAAACAAGAACGTACAATGTACGGAACTCGAC
A

Using a simple cycle of all four nucleotides, each of these would take, respectively, 84, 72, and 100 nucleotides to complete sequencing. Using an optimised sequence, ACTGACTGACGTACGTATCGACTAGTCAGTACAGT-GACTGACTACGTACTGATCG ATCGATCGTCGATC-GAT, sequencing of all target sequences could be completed in 72 nucleotides.

An example of the optimisation process is given as follows. Note that this is merely one example; other algorithms can be used, and it is possible that such other algorithms would provide a greater degree of optimisation.

In outline, the algorithm looks at the next base to be sequenced in each of the DNA strands, and picks the one that is most likely to occur. If there are two or more bases equally likely to crop up, it picks the base that has been waiting longest to be flowed.

As a starting point for describing the algorithm, suppose we want to sequence a sample which we believe contains one of the following DNA sequences:

Sequence 1:
ACTCTACTAACGTATGGCTACCCTTAGTGGGGATGCTACCTAAAACCCTT
C

Sequence 2:
CGAATGAGTATCTTATTACCATTTTGCAGTCCAATGTTTTAATTGTGTTG
T

Sequence 3:
ATACGACGCATACGGTTCGAAACAAGAACGTACAATGTACGGAACTCGAC
A

For each sequence, the algorithm maintains a pointer to the next base to be sequenced. In the details below, these pointers are represented as arrows underneath each sequence. The following sections show the first ten steps of the algorithm to illustrate how it works.

Flow Step 1

Before the first nucleotide flows, the current positions in each sequence are as shown below:

Sequence 1
ACTCTACTAACGTATGGCTACCCTTAGTGGGGATGCTACCTAAAACCCTT
C^

Sequence 2
CGAATGAGTATCTTATTACCATTTTGCAGTCCAATGTTTTAATTGTGTTG
T^

Sequence 3
ATACGACGCATACGGTTCGAAACAAGAACGTACAATGTACGGAACTCGAC
A^

In this case two of the sequences are A and one is C. Therefore the first nucleotide to flow will be A, as this is more likely to give an extension.

Flow Step 2

Before this nucleotide flows, the current positions in each sequence are as shown below:

Sequence 1
ACTCTACTAACGTATGGCTACCCTTAGTGGGGATGCTACCTAAAACCCTT
C_^

Sequence 2
CGAATGAGTATCTTATTACCATTTTGCAGTCCAATGTTTTAATTGTGTTG
T^

Sequence 3
ATACGACGCATACGGTTCGAAACAAGAACGTACAATGTACGGAACTCGAC
A_^

In this case, two of the nucleotides are C and one is T. The algorithm chooses C, as this is most likely to give an extension.

Flow Step 3

Before this nucleotide flows, the current positions in each sequence are as shown below:

Sequence 1
ACTCTACTAACGTATGGCTACCCTTAGTGGGGATGCTACCTAAAACCCTT
C^

Sequence 2
CGAATGAGTATCTTATTACCATTTTGCAGTCCAATGTTTTAATTGTGTTG
T_^

Sequence 3
ATACGACGCATACGGTTCGAAACAAGAACGTACAATGTACGGAACTCGAC
A_^

In this case, two of the nucleotides are T and one is G. The algorithm chooses T, as this is most likely to give an extension.

Flow Step 4

Before this nucleotide flows, the current positions in each sequence are as shown below:

Sequence 1
ACTCTACTAACGTATGGCTACCCTTAGTGGGGATGCTACCTAAAACCCTT
C_^

Sequence 2
CGAATGAGTATCTTATTACCATTTTGCAGTCCAATGTTTTAATTGTGTTG
T_^

Sequence 3
ATACGACGCATACGGTTCGAAACAAGAACGTACAATGTACGGAACTCGAC
A_^

In this case, the three nucleotides C, G, and A are all equally likely. The nucleotide waiting longest is G, and so this is chosen as the nest nucleotide in the sequence.

Flow Step 5

Before this nucleotide flows, the current positions in each sequence are as shown below:

Sequence 1
ACTCTACTAACGTATGGCTACCCTTAGTGGGGATGCTACCTAAAACCCTT
C_^

Sequence 2
CGAATGAGTATCTTATTACCATTTTGCAGTCCAATGTTTTAATTGTGTTG
T_^

Sequence 3
ATACGACGCATACGGTTCGAAACAAGAACGTACAATGTACGGAACTCGAC
A_^

In this case nucleotide A is most likely so this is chosen.

Flow Step 6

Before this nucleotide flows, the current positions in each sequence are as shown below:

Sequence 1
ACTCTACTAACGTATGGCTACCCTTAGTGGGGATGCTACCTAAAACCCTT
C_^

Sequence 2
CGAATGAGTATCTTATTACCATTTTGCAGTCCAATGTTTTAATTGTGTTG
T_^

Sequence 3
ATACGACGCATACGGTTCGAAACAAGAACGTACAATGTACGGAACTCGAC

A_^

In this case nucleotide c is most likely, so we choose this.
Flow Step 7
Before this nucleotide flows, the current positions in each sequence are as shown below:

Sequence 1
ACTCTACTAACGTATGGCTACCCTTAGTGGGGATGCTACCTAAAACCCTT

C_^

Sequence 2
CGAATGAGTATCTTATTACCATTTTGCAGTCCAATGTTTTAATTGTGTTG

T_^

Sequence 3
ATACGACGCATACGGTTCGAAACAAGAACGTACAATGTACGGAACTCGAC

A_^

In this case nucleotide T is most likely, so we choose this.
Flow Step 8
Before this nucleotide flows, the current positions in each sequence are as shown below:

Sequence 1
ACTCTACTAACGTATGGCTACCCTTAGTGGGGATGCTACCTAAAACCCTT

C_^

Sequence 2
CGAATGAGTATCTTATTACCATTTTGCAGTCCAATGTTTTAATTGTGTTG

T_^

Sequence 3
ATACGACGCATACGGTTCGAAACAAGAACGTACAATGTACGGAACTCGAC

A_^

In this case nucleotide G is most likely, so we choose this.
Flow Step 9
Before this nucleotide flows, the current positions in each sequence are as shown below:

Sequence 1
ACTCTACTAACGTATGGCTACCCTTAGTGGGGATGCTACCTAAAACCCTT

C_^

Sequence 2
CGAATGAGTATCTTATTACCATTTTGCAGTCCAATGTTTTAATTGTGTTG

T_^

Sequence 3
ATACGACGCATACGGTTCGAAACAAGAACGTACAATGTACGGAACTCGAC

A_^

In this case, all sequences require nucleotide A, so we choose this.
Flow Step 10
Before this nucleotide flows, the current positions in each sequence are as shown below:

Sequence 1
ACTCTACTAACGTATGGCTACCCTTAGTGGGGATGCTACCTAAAACCCTT

C_^

Sequence 2
CGAATGAGTATCTTATTACCATTTTGCAGTCCAATGTTTTAATTGTGTTG

T_^

Sequence 3
ATACGACGCATACGGTTCGAAACAAGAACGTACAATGTACGGAACTCGAC

A_^

In this case nucleotide C is most likely, so this is chosen.

In many applications it would be beneficial to combine several of the above methods of implementation. For example, in a bloodstream infection tool, a probabilistic algorithm could predict the most likely infectious agent. By predicting the sequence of several 16S amplicons, an optimised flow pattern could be determined. If, during the test, the predicted infectious agent turns out to be incorrect, an intelligent adaptive flow could adjust the optimal nucleotide flow pattern based on a revised probabilistic algorithm.

Given the constraints on determining an optimal flow sequence for multiple target sequences, the various aspects of the invention are likely to be mainly suited for situations in which only one or a small number of sequences are likely to be present.

The invention claimed is:

1. A method for sequencing a polynucleotide strand by sequencing by synthesis, the method comprising the steps of:
   a) providing in a reaction a polynucleotide strand to be sequenced, a primer, and a polymerase enzyme;
   b) providing to the reaction nucleotides in a predetermined order, wherein the predetermined order is selected to correlate with a predicted sequence for the polynucleotide strand;
   c) monitoring the reaction to detect incorporation of a nucleotide into a synthesised polynucleotide strand;
   wherein, in the event that nucleotide incorporation is detected, proceeding to provide the next nucleotide in the predetermined order.

2. The method of claim 1, wherein, in the event that nucleotide incorporation is not detected, the predicted sequence for the polynucleotide strand is revised and a new predetermined order of nucleotides selected, wherein the new predetermined order is selected to correlate with the revised predicted sequence.

3. The method of claim 1, wherein, in the event that nucleotide incorporation is not detected, a new predetermined order of nucleotides is selected which represents multiple cycles of all four nucleotides.

4. The method of claim 1, wherein, in the event that nucleotide incorporation is not detected, the reaction is stopped.

5. The method of claim 2, comprising the step of determining the initial relative likelihood of a plurality of predicted sequences, and selecting the initial predicted sequence to be the most likely of the plurality of predicted sequences.

6. The method of claim 5, further comprising the step of, when revising the predicted sequence, selecting the next most likely of the plurality of predicted sequences as the revised predicted sequence.

7. The method of claim 2, wherein the step of monitoring the reaction to detect incorporation of a nucleotide also includes, in the event that incorporation is detected, adding data representing that nucleotide to recorded sequence data representing the polynucleotide to be sequenced.

8. The method of claim 7, wherein the step of revising the predicted sequence data includes comparing the recorded sequence data to polynucleotide sequence data stored in a database, and selecting the most likely candidate sequence from the database matching the recorded sequence data as a revised predicted sequence.

9. The method of claim 1, further comprising, prior to step (b), providing multiple different nucleotides to the reaction simultaneously.

10. The method of claim 9, wherein the multiple different nucleotides lack one, or two, of the four nucleotides A, G, C, T.

11. The method of claim 9, wherein multiple rounds of providing multiple different nucleotides are used.

12. The method of claim 1, wherein the predetermined order of nucleotides is selected to correlate with predicted sequences for two or more different polynucleotides to be sequenced.

13. The method of claim 12, wherein the order of nucleotides is selected to allow efficient sequencing of each of the two or more different polynucleotide sequences.

14. A method for sequencing a polynucleotide strand by sequencing by synthesis, the method comprising the steps of:
   a) providing in a reaction a polynucleotide strand to be sequenced, a primer, and a polymerase enzyme;
   b) providing to the reaction multiple different nucleotides simultaneously, wherein the multiple different nucleotides lack at least one of the four nucleotides A, C, G T;
   c) subsequently providing to the reaction nucleotides in a predetermined order, wherein the predetermined order is selected to correlate with a predicted sequence for the polynucleotide strand;
   d) monitoring the reaction to detect incorporation of the nucleotides of the predetermined order into a synthesised polynucleotide strand; and
   e) in the event that nucleotide incorporation is detected, proceeding to provide the next nucleotide in the predetermined order.

15. The method of claim 14, further comprising the step of:
   f) in the event that nucleotide incorporation is not detected, revising the predicted sequence for the polynucleotide strand and selecting a new predetermined order of nucleotides, wherein the new predetermined order is selected to correlate with the revised predicted sequence.

16. The method of claim 14, further comprising the step of:
   f) in the event that nucleotide incorporation is not detected, revising the predicted sequence for the polynucleotide strand and selecting a new predetermined order of nucleotides which represents multiple cycles of all four nucleotides.

17. The method of claim 14, further comprising the step of:
   f) in the event that nucleotide incorporation is not detected, stopping the reaction.

* * * * *

SEQUENCE LISTING

<160> NUMBER OF SEQ ID NOS: 20

<210> SEQ ID NO 1
<211> LENGTH: 37
<212> TYPE: DNA
<213> ORGANISM: Artificial Sequence
<220> FEATURE:
<223> OTHER INFORMATION: hypothetical sequence

<400> SEQUENCE: 1
gcacctgtct cagagttccc gaaggcacca aagcatc     37

<210> SEQ ID NO 2
<211> LENGTH: 14
<212> TYPE: DNA
<213> ORGANISM: Artificial Sequence
<220> FEATURE:
<223> OTHER INFORMATION: hypothetical sequence

<400> SEQUENCE: 2
cgtggacaga gtgc                                                             14

<210> SEQ ID NO 3
<211> LENGTH: 14
<212> TYPE: DNA
<213> ORGANISM: Artificial Sequence
<220> FEATURE:
<223> OTHER INFORMATION: hypothetical sequence

<400> SEQUENCE: 3
cgtggacaga gtgt                                                             14

<210> SEQ ID NO 4
<211> LENGTH: 32
<212> TYPE: DNA
<213> ORGANISM: Artificial Sequence
<220> FEATURE:
<223> OTHER INFORMATION: hypothetical sequence

<400> SEQUENCE: 4
cgtggacaga gtgtcaaggg cttccgtggt ta                                         32

<210> SEQ ID NO 5
<211> LENGTH: 32
<212> TYPE: DNA
<213> ORGANISM: Artificial Sequence
<220> FEATURE:
<223> OTHER INFORMATION: hypothetical sequence

<400> SEQUENCE: 5
cgtggacaga gtgtcaaggg cttccgtggt tc                                         32

<210> SEQ ID NO 6
<211> LENGTH: 37
<212> TYPE: DNA
<213> ORGANISM: Artificial Sequence
<220> FEATURE:
<223> OTHER INFORMATION: hypothetical sequence

<400> SEQUENCE: 6
cgtggacaga gtctcaaggg cttccgtggt ttcgtag                                    37

<210> SEQ ID NO 7
<211> LENGTH: 32
<212> TYPE: DNA
<213> ORGANISM: Artificial Sequence
<220> FEATURE:
<223> OTHER INFORMATION: hypothetical sequence

<400> SEQUENCE: 7
cacctgtcac tctactaacg tatggctacc ct                                         32

<210> SEQ ID NO 8
<211> LENGTH: 32
<212> TYPE: DNA
<213> ORGANISM: Artificial Sequence
<220> FEATURE:
<223> OTHER INFORMATION: hypothetical sequence

<400> SEQUENCE: 8
cacctgtccg aatgagtatc ttattaccat tg                                         32

<210> SEQ ID NO 9

```
<211> LENGTH: 32
<212> TYPE: DNA
<213> ORGANISM: Artificial Sequence
<220> FEATURE:
<223> OTHER INFORMATION: hypothetical sequence

<400> SEQUENCE: 9
cacctgtcat acgacgcata cggttcgaaa ca                          32

<210> SEQ ID NO 10
<211> LENGTH: 51
<212> TYPE: DNA
<213> ORGANISM: Artificial Sequence
<220> FEATURE:
<223> OTHER INFORMATION: hypothetical sequence

<400> SEQUENCE: 10
actctactaa cgtatggcta cccttagtgg ggatgctacc taaaaccctt c     51

<210> SEQ ID NO 11
<211> LENGTH: 51
<212> TYPE: DNA
<213> ORGANISM: Artificial Sequence
<220> FEATURE:
<223> OTHER INFORMATION: hypothetical sequence

<400> SEQUENCE: 11
cgaatgagta tcttattacc attttgcagt ccaatgtttt aattgtgttg t     51

<210> SEQ ID NO 12
<211> LENGTH: 51
<212> TYPE: DNA
<213> ORGANISM: Artificial Sequence
<220> FEATURE:
<223> OTHER INFORMATION: hypothetical sequence

<400> SEQUENCE: 12
atacgacgca tacggttcga aacaagaacg tacaatgtac ggaactcgac a     51

<210> SEQ ID NO 13
<211> LENGTH: 72
<212> TYPE: DNA
<213> ORGANISM: Artificial Sequence
<220> FEATURE:
<223> OTHER INFORMATION: hypothetical sequence

<400> SEQUENCE: 13
actgactgac gtacgtatcg actagtcagt acagtgactg actacgtact gatcgatcga   60
tcgtcgatcg at                                                       72

<210> SEQ ID NO 14
<211> LENGTH: 51
<212> TYPE: DNA
<213> ORGANISM: Artificial Sequence
<220> FEATURE:
<223> OTHER INFORMATION: hypothetical sequence

<400> SEQUENCE: 14
actctactaa cgtatggcta cccttagtgg ggatgctacc taaaaccctt c     51

<210> SEQ ID NO 15
<211> LENGTH: 51
<212> TYPE: DNA
<213> ORGANISM: Artificial Sequence
<220> FEATURE:
<223> OTHER INFORMATION: hypothetical sequence
```

```
<400> SEQUENCE: 15
cgaatgagta tcttattacc attttgcagt ccaatgtttt aattgtgttg t          51

<210> SEQ ID NO 16
<211> LENGTH: 51
<212> TYPE: DNA
<213> ORGANISM: Artificial Sequence
<220> FEATURE:
<223> OTHER INFORMATION: hypothetical sequence

<400> SEQUENCE: 16
atacgacgca tacggttcga aacaagaacg tacaatgtac ggaactcgac a          51

<210> SEQ ID NO 17
<211> LENGTH: 72
<212> TYPE: DNA
<213> ORGANISM: Artificial Sequence
<220> FEATURE:
<223> OTHER INFORMATION: hypothetical sequence

<400> SEQUENCE: 17
actgactgac gtacgtatcg actagtcagt acagtgactg actacgtact gatcgatcga 60
tcgtcgatcg at                                                     72

<210> SEQ ID NO 18
<211> LENGTH: 51
<212> TYPE: DNA
<213> ORGANISM: Artificial Sequence
<220> FEATURE:
<223> OTHER INFORMATION: hypothetical sequence

<400> SEQUENCE: 18
actctactaa cgtatggcta cccttagtgg ggatgctacc taaaacccctt c         51

<210> SEQ ID NO 19
<211> LENGTH: 51
<212> TYPE: DNA
<213> ORGANISM: Artificial Sequence
<220> FEATURE:
<223> OTHER INFORMATION: hypothetical sequence

<400> SEQUENCE: 19
cgaatgagta tcttattacc attttgcagt ccaatgtttt aattgtgttg t          51

<210> SEQ ID NO 20
<211> LENGTH: 51
<212> TYPE: DNA
<213> ORGANISM: Artificial Sequence
<220> FEATURE:
<223> OTHER INFORMATION: hypothetical sequence

<400> SEQUENCE: 20
atacgacgca tacggttcga aacaagaacg tacaatgtac ggaactcgac a          51
```